United States Patent
Staal et al.

(10) Patent No.: US 10,830,748 B2
(45) Date of Patent: Nov. 10, 2020

(54) PROCESS AND APPARATUS FOR SCRAP METAL SCANNING

(71) Applicant: ScrapScanner B.V., Haerderwijk (NL)

(72) Inventors: Hendrikus Staal, Harderwijk (NL); Martijn Van de Poll, Harderwijk (NL); Simon Petrus Maria Berkhout, Harderwijk (NL); Peter Carlo Rem, Harderwijk (NL)

(73) Assignee: SCRAPSCANNER B.V., Harderwijk (NL)

( * ) Notice: Subject to any disclaimer, the term of this patent is extended or adjusted under 35 U.S.C. 154(b) by 0 days.

(21) Appl. No.: 16/349,006

(22) PCT Filed: Nov. 13, 2017

(86) PCT No.: PCT/NL2017/050732
§ 371 (c)(1),
(2) Date: May 10, 2019

(87) PCT Pub. No.: WO2018/088905
PCT Pub. Date: May 17, 2018

(65) Prior Publication Data
US 2019/0277825 A1    Sep. 12, 2019

(30) Foreign Application Priority Data
Nov. 11, 2016 (NL) ...................... 2017769

(51) Int. Cl.
*G01N 21/00*     (2006.01)
*G01N 33/202*    (2019.01)
(Continued)

(52) U.S. Cl.
CPC ........... *G01N 33/202* (2019.01); *C22B 1/005* (2013.01); *G01N 21/718* (2013.01); *G01N 21/85* (2013.01);
(Continued)

(58) Field of Classification Search
CPC .... G01N 33/202; G01N 21/85; G01N 21/718; G01N 23/204; G01N 27/72; G01N 2021/8592; C22B 1/005; Y02P 10/212
See application file for complete search history.

(56) References Cited

U.S. PATENT DOCUMENTS 5,948,137 A * 9/1999 Pflaum ................. C21C 5/4673
266/100
2009/0236268 A1  9/2009 Shulman
2009/0261981 A1  10/2009 Jones et al.

FOREIGN PATENT DOCUMENTS

DE        2138540 A1    2/1973
DE   102010028270 A1   10/2011
(Continued)

OTHER PUBLICATIONS

Peter et al. "Liquid steel analysis with laser-induced breakdown spectrometry in the vacuum ultraviolet." Applied Optics 42.30 (2003): 6199-6204.
(Continued)

*Primary Examiner* — Abdullahi Nur
(74) *Attorney, Agent, or Firm* — Leason Ellis LLP

(57) ABSTRACT

The invention is direct to a method and an apparatus for the bulk determination of scrap metal content, said method comprising the steps of providing a scrap metal input; preparing said input for submission to a bulk scanning apparatus; scanning at least part of the scrap metal with a bulk scanning apparatus to determine the composition of the scrap metal; and securing said scrap metal from the step of providing the scrap metal input to the step of scanning at least part of the scrap metal. Said apparatus comprises a scanning container together with a low-intensity neutron scattering device, a laser cutting device and/or magnetic sensing device.

17 Claims, 5 Drawing Sheets

(51) Int. Cl.
*C22B 1/00* (2006.01)
*G01N 21/71* (2006.01)
*G01N 23/204* (2006.01)
*G01N 27/72* (2006.01)
*G01N 21/85* (2006.01)

(52) U.S. Cl.
CPC ........... *G01N 23/204* (2013.01); *G01N 27/72* (2013.01); *G01N 2021/8592* (2013.01); *Y02P 10/212* (2015.11)

(56) References Cited

FOREIGN PATENT DOCUMENTS

| WO | 0005423 A1 | 2/2000 |
|---|---|---|
| WO | WO01/07888 A2 | 2/2001 |
| WO | 2012093256 A2 | 7/2012 |

OTHER PUBLICATIONS

Carlhoff. "Laser technology for C measurement." Steel Times International 16.4 (1992): 36.
International Search Report and Written Opinion in corresponding International Patent Application No. PCT/NL2017/050732 dated Jun. 21, 2018. 17 pages.
Roger Pynn; "Introduction & Neutron Scattering Theory", Dec. 21, 1997 (Dec. 21, 1997), Retreived from the internet: url:https//neutrons.ornl.gov/sites/default/files/intro_to_neutron_scattering.pdf (retreived on Mar. 4, 2020).
European Office Action in Corresponding EP Application No. 17817233.4 dated Mar. 16, 2020. 6 pages.

\* cited by examiner

PROCESS AND APPARATUS FOR SCRAP METAL SCANNING

CROSS-REFERENCE TO RELATED PATENT APPLICATIONS

This application is a U.S. National Stage Application under 35 U.S.C. § 371 of International Patent Application No. PCT/NL2017/050732, filed Nov. 13, 2017, which claims the benefit of priority under 35 U.S.C. Section 119(e) of Netherlands Patent Application number NL 2017769 filed Nov. 11, 2016, both of which are incorporated by reference in their entireties. The International Application was published on May 17, 2018, as International Publication No. WO 2018/088905 A2.

The invention is directed to the handling of scrap metal. The invention is particularly directed to the determination and securing of the composition and the handling of scrap metal.

Scrap metal is an important resource for recyclable metals. Scrap metal is typically collected by scrap metal collectors from many different sources. Scrap metal may include manufacturing leftovers or used products, such as vehicle parts, building parts, electronic devices and the like. Due to the different origins of scrap metal, its composition may vary for each batch. This means that the types as well as amount of valuable metals can vary. In addition, the scrap metal may also contain plastics and other non-metallic components such as moisture, oil and minerals as contaminants.

Accordingly, before the scrap metal is submitted to the melting process or is traded from one party the another (since the composition of the scrap metal influences its market value), it is required that the composition of the scrap metal is determined as this may vary depending on the origin of the scrap metal.

Conventional methods to determine the composition of scrap metal include visual inspection by a trained expert. The trained expert assesses the composition of a batch of scrap metal by eye in a so called 'eyeballing' process. Although the trained expert may utilize handheld scanning apparatus and/or by manually taking small samples for laboratory analysis, this manual procedure is tedious and sensitive to errors for a variety of reasons. For instance, since the scrap metal is typically provided on a heap or stack, certain parts of the scrap metal may be located out of the line-of-sight of the trained expert which may result in that a significant part of the scrap metal is not taken into account when its composition is determined. In addition, certain pieces of the scrap metal may be coated with a coating which composition is not representative for the entire scrap metal pieces. Moreover, the experience and/or interest of the trained expert may erroneously influence his assessment of the composition of the scrap metal. Also, the composition of a scrap metal batch may be altered due to external factors in the time between the scrap metal is provided (e.g. unloaded from the supply truck or container) and scanned. Examples thereof include change of the moisture content, e.g. due to rain, or (un)intentional mixing of a batch with other scrap metal parts to influence the market value of the batch. In practice, this leads to discussion between parties on the correctness on the assessment, reassessments being carried out, and discussion on which assessment should be accepted.

In WO 00/05423, a scrap metal weighing and online bulk material analysis process and apparatus is disclosed. A drawback of the process and apparatus described herein is that possible alteration of the scrap metal after scanning may not be detected.

US 2009/0261981 discloses a process comprising the weighting of scrap metal in a secured contained to determine the value of the scrap metal. A drawback of this process is the inaccuracy of merely weighting the scrap metal as this can not provide information regarding the content of different metals in the scrap metal.

An object of the present invention is accordingly to provide a reliable and improved method for determining the composition of scrap metal to address at least part of the above-described drawbacks of the conventional methods.

An aspect of the present invention is therefore a method for the bulk determination of scrap metal content, said method comprising the steps of
  providing a scrap metal input;
  preparing said input for submission to a bulk scanning apparatus;
  scanning at least part of the scrap metal with a bulk scanning apparatus to determine the composition of the scrap metal;
wherein said scrap metal is secured from the step of providing the scrap metal input to the step of scanning at least part of the scrap metal.

Advantageously, the combination of using a bulk scanning device and the securing of the scrap metal improves the reliably of the bulk determination of scrap metal composition. Bulk scanning is advantageous when compared to a random samples scanning procedure as essentially the entire batch is scanned. This greatly reduces or even removes the risk of only scanning a part of the scrap metal that is not representative for the entire batch. Bulk scanning thus provides more precise, more accurate and better reproducible scanning results, not only when compared to the eyeballing process but also when compared to random samples scanning assisted by scanning devices.

The securing of the scrap metal may serve multiple purposes. By securing the scrap metal, undetected tampering of the scrap metal may be prevented. For certain parties involved in the handling of the scrap metal, it may be beneficial to tamper with the scrap metal and change its composition and alleged value. This may result in disputes between different parties that handle the scrap metal. The securing of the scrap metal thus may also serve to prevent such disputes. In addition, or alternatively, in case the composition of the scrap metal is believed to be altered at some point in the process, the securing of the scrap metal may allow to trace back the point on which the alteration took place and analyze the effect of the alteration on the composition. This may result in an improved determination of the value of the scrap metal.

Securing the scrap metal can comprise safeguarding the scrap metal against undetected tampering, for instance safe keeping the scrap metal in a sealed room or container, monitoring the scrap metal, tagging or labeling the scrap metal, monitoring the environment of the scrap metal, etcetera, or a combination thereof.

Monitoring the scrap metal preferably comprises visually monitoring the scrap metal, which is more preferably carried out by a camera system of which the images are stored such that these may be accessed to assess whether the composition of the scrap metal was changed in time. In addition, the visual monitoring may comprise real-time monitoring with a camera system in combination with storing the recorded data in an archive such that the results of the monitoring (i.e. data such as images) can be accessed after the scrap metal has been handled (e.g. delivered, scanned and transported). Preferably, any party associated in the handling and trading of the scrap metal can be allowed to have access to the real-time monitoring and/or the stored recorded data.

The present method is a transparent method, meaning that the relevant aspects of the method and the handling of scrap metal is verifiable by a third party (e.g. a scrap metal supplier or smelter vis-à-vis a scrap metal trader) without the necessity to repeat the scrap metal content determination. The present method may increase the trust that the third party places in values that are not determined by that same third party, thereby reducing the requirement of additional analytical methods of the same type that merely serve to confirm earlier found values. The present method thus advantageously renders the overall handling of scrap metal from source to smelter more efficient.

Accordingly, in a preferred embodiment of the present invention, the present method is certified by an analytical certificate to ensure the reliability of the method. The certification of the method can be carried out by an independent party.

The present method may be applied by i.a. scrap metal traders and/or scrap metal smelters. For scrap metal traders, a batch of scrap metal is typically provided by a supply truck after which the scrap metal may be subjected to the bulk scanning apparatus. Subsequently, the scanned scrap metal is loaded into a container for transport. Preferably, the container is sealed and offered for transport directly after loading. For sake of reliability of the present method, it is preferred that the scrap metal is also secured, preferably visually monitored, from the step of scanning to the step of loading the scrap metal into the container, preferably up to the point that the container reaches the subsequent handler in the overall scrap metal handling process or supply chain (e.g. the smelter).

For scrap metal smelters which receive the scrap metal from e.g. scrap metal traders, the scrap metal is typically provided in the containers. For scrap metal smelters, it may be preferred—although not necessarily required, in particular if the content has been determined by a previous handler such as a scrap metal trader—that before submitting the scrap metal to the smelting process, the content of the scrap metal is verified by a scanning step in accordance with the present method. It may even more be preferred that the method further comprises comparing the composition of the scrap metal as determined in the scanning step with the composition of the scrap metal as determined in a separate previous scanning step. In a yet even more preferred embodiment, the separate previous scanning step was carried out using a scanning apparatus of the same type as said bulk scanning apparatus, for instance with a substantially identical bulk scanning apparatus and/or a bulk scanning apparatus that is calibrated with the same calibration method. This particular embodiment of the present invention is particularly advantageous to trace and analyze discrepancies between two or more separate scrap metal content determination and/or to prevent undesired disputes between parties involved in the handling of scrap metal.

Preferably, all steps of the method in accordance with the present invention are physically connected which means that the method preferably includes the logging and handling of individual and uniquely identifiable batches of the scrap metal. Typically, a batch of scrap metal that arrives by a supply truck is loaded entirely ill the scanning container, scanned and loaded in a transportation container. As such, the origin and composition of a scrap metal batch upon delivery of the transportation can be traced back to the scrap metal as delivered by the supply truck. Conventional processes are generally not physically connected and different scrap metal batches can be mixed and divided before trading. As such, the batches of scrap metal in these conventional processes are not handled individually and can not be identified uniquely. This decreases reliability of the scrap metal composition determination.

A particular aspect of the present invention is the step of preparing said input, which step comprises reorganizing said input to obtain a substantially predictable reorganized arrangement comprising the scrap metal. Scrap metal typically comprises pieces of different sizes and the differently sized pieces typically also differ in the composition. To determine the composition of the scrap metal, a number of measurements are typically to be taken (vide infra). To ensure that these measurements are representative of the overall (average) scrap metal composition, it is preferred that the measurements are not only taken from particularly sized pieces (e.g. the largest pieces) but from a representative selection of the pieces. It is therefore preferable that the scrap metal is organized in an arrangement that enables scanning of a representative selection of the pieces. It may be appreciated that the precise arrangement of the scrap metal pieces may depend on the size and shape distribution of the scrap metal pieces. However, particular reorganization steps may result in a predictable organized arrangement to which the scanning method may be adjusted.

Accordingly, segregation of different scrap metal pieces based on their size before the scrap metal is scanned is preferably limited. In addition, any effect that is associated with a particular non-homogenous organization of the scrap metal as provided is preferably prevented, more preferably annulled. Scrap metal as is it for instance provided by truck load, may be organized within the truck in a non-homogeneous manner which may result in non-representative scanning of the scrap metal. This non-representative scanning is preferably is limited or prevented by the step of preparing said input for submission to a bulk scanning apparatus.

Preferably, the step of preparing said input for submission to a bulk scanning apparatus comprises, optionally repeatedly, re-loading the scrap metal on a heap, thereby destroying and randomizing the original distribution or organization of the scrap metal and allowing the scrap metal to segregate according to a pattern that can be assessed/interpreted by scanning the batch of scrap metal from all sides. The scrap metal input is thus preferably reoriented such that it is arranged in a favorable orientation or organization for the bulk scanning step. By this reorientation, for instance by arranging the scrap metal batch such that a larger surface area can be accessed by the scanning device, the scrap metal may become more accessible for the bulk scanning device.

In a particular embodiment of the present invention, the scrap metal input is arranged in a scanning container, preferably a cylinder shaped container, by dropping the scrap metal from a predefined height into said scanning container.

Additionally or alternatively, the scrap metal input may be reorganizing onto a conveyer belt, although this may not necessary be preferred as smaller pieces, dust and/or moisture tend to end up on the surface of the belt which hampers the scanning of these smaller pieces. In a preferred embodiment, the scrap metal input is therefore first loaded onto a conveyer belt and subsequently dropped into the scanning container.

A particularly practical embodiment comprises unloading the input scrap metal (e.g. from a truck) onto a conveyor with a length that is essentially larger than the length of entire batch of input scrap metal as provided (e.g. the length of the container of the truck). This may typically be followed by compacting the scrap metal by loading (e.g. dropping or throwing) the scrap metal with a particular motion (e.g. a swirling or rotating motion) from the conveyor into a scanning container, preferably a cylinder-shaped scanning container, that preferably has a height that is essentially shorter than the length of the conveyor. This repeated re-loading randomizes the material and produces a natural segregation.

BRIEF DESCRIPTION OF THE DRAWINGS

A particular embodiment of loading scrap metal in the scanning container in accordance with the present invention is illustrated in FIGS. 1 and 2. In FIGS. 1 (top view) and 2 (perspective view), the scanning container (1) is loaded with scrap metal pieces (3) that are transported by conveyer (2) towards the scanning container (1) and dropped into the internal space (10 of the scanning container. The end of the conveyer (2) from which the scrap metal pieces drop into the conveyer may move in a rotating or swirling motion with respect the scanning container, as indicated with a solid circular arrow (6). In a particular embodiment, one or more scanning devices (4) may rotate with respect to the scanning container, as indicated with the dashed circular arrow (5). It may be appreciated that the scanning container may also rotate around its longitudinal (horizontal) axis in addition or alternatively to the rotating motion of the end of the conveyer or the rotating scanning apparatus.

Figure 1:
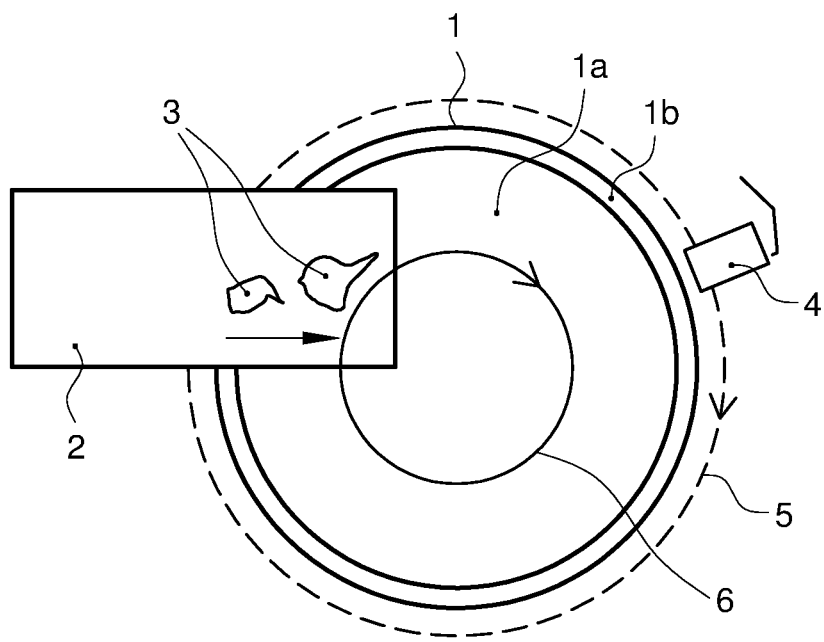
FIG. 1 shows the top view of an embodiment of the scanning container.

A particular aspect of the present invention is directed to an improved bulk scanning method. Scrap metal may comprise ferrous scrap metal, non-ferrous scrap metal or a combination thereof. Examples of valuable method from non-ferrous scrap metal include copper, tin, aluminum, zinc, lead, brass, bronze and the like. Non-ferrous scrap metal may comprise electric motors (comprising copper coils), electric cables (comprising copper), stainless steel (comprising chromium and/or nickel), and the like. Examples of types of ferrous scrap metal include heavy melting steel (HMR), cut iron, shards, new shards, sheet iron, iron bars, iron turnings, cast iron, and the like.

The scrap metal may further comprise one or more contaminants selected from the group consisting of moisture, plastics, oil, steel, minerals or combinations thereof.

The presence of minerals is preferably prevented as this is typically detrimental to the smelting process. Typical minerals of which the presence and amount may be determined by the present invention are calcium- and/or silica-comprising minerals such as stone and sand.

The bulk scanning method enables to determine the ferrous and/or non-ferrous metal content versus contaminants content. Preferably, the bulk scanning method enables determining the amount of each type of component present in the scrap metal.

In a particular embodiment of the present invention, the scanning at least part of the scrap metal with a bulk scanning apparatus comprises cutting, such as mechanical or laser cutting, magnetic sensing, low-intensity neutron scattering, or a combination thereof, preferably mechanical and laser cutting, more preferably mechanical and laser cutting in combination with magnetic sensing and low-intensity neutron scattering.

Magnetic sensing enables determining the amount of (ferromagnetic) metallic material, particularly steel, in the scrap metal. Magnetic sensing in accordance with the present invention may be carried out by placing the scrap metal in a magnetic field that typically ranges from 5 to 100 Gauss, preferably 10 to 40 Gauss as typically created with a permanent magnet. The metallic content of the scrap metal results in a quantitatively detectable change of the magnetic field. The change may for instance be detected by one or more Hall sensors. For the purpose of magnetic sensing, it is preferred that the scanning container as described herein above, is based on non-magnetic material such as aluminum or austenitic steel.

Low-intensity neutron scattering enables determining the amount of hydrogen-containing materials such as moisture, oil and plastics. Low-intensity neutron scattering is a technique known to for instance measure moisture content in soil (see e.g. U.S. Pat. No. 4,864,142A). The inventors found that low-intensity neutron scattering is particularly suitable for analyzing non-metallic components in scrap metal, since neutron radiation relatively easily passes through metal (particularly readily through aluminum) but is strongly scattered by hydrogen atoms. Low-intensity neutron scattering is thus particularly suitable to analyze parts of the scrap metal that are located within a three-dimensionally arrangement of scrap metal (e.g. a stack or heap of scrap metal or scrap metal placed in a container) and accordingly obstructed from sight.

The back-scattering signal is substantially proportional to the average volumetric concentration (and thus mass) of hydrogen atoms within the scrap metal. The detected mass of hydrogen atoms can be correlated to the mass of water and hydrocarbons such as polyethylene by multiplying the detected mass of hydrogen with a multiplication factor 7 or 9 respectively. The multiplication factor is based on the weight ratio of hydrogen-atoms versus all other atoms in the material and may differ per material. The accuracy of the low-intensity scattering can be increased by using a multiplication factor which is i.a. based on parameters that are obtained by securing, e.g. visually monitoring, the scrap metal.

Other parameters that may be used to increase the accuracy of the low-intensity scattering and to establish the multiplication factor include the source category of the scrap metal (e.g. zorba, electric cable and the like) and the distribution of the neutron back-scattering intensity as a function of the angle of the neutron feeding direction since this distribution is higher for a high moisture content. The visually monitoring can thus also increase the accuracy of the scrap metal determination by the bulk scanning step.

The cutting of the scrap metal can be applied to access and scan part of the scrap metal that is located within the bulk of the scrap metal and therefore otherwise obstructed from sight upon visual inspection of the scrap metal. The cutting thus allows the scanning of a part of scrap metal that would not be included in the determination of the scrap metal content by eye-balling. The cutting of scrap metal can be carried out mechanically by using a mechanical cutter such as a grinding machine, by laser cutting or by a combination thereof.

A preferred embodiment comprises a combination of mechanical cutting and laser cutting. For instance, an initial cut can be created with mechanical cutting (e.g. up to about 10 cm into the scrap metal bulk), followed by laser cutting that preferably includes the determination of the scrap metal composition by laser-induced breakdown spectroscopy. It may be appreciated that in particular for this preferred embodiment, cutting with the laser may essentially only serve to scan the composition of the scrap metal (vide infra) and as such the depth of the created cut by the laser can be limited with respect to the cut created by the initial mechanical cutting.

Laser cutting is based on using a laser to cut part of the scrap metal and possibly also determine both the scrap metal composition and volume of scrap metal that has been cut away by the laser.

The composition of the scrap metal can be determined by laser cutting which leads to the formation of fire and/or a particle mist. Although the formation of the fire and particle mist can thus advantageously be used in accordance with the present invention (vide infra), excessive fire and particle mist formation is not preferred due to possibly associated safety and health risk. A particular advantage from combining initial mechanical cutting and subsequent laser cutting is that the fire and excessive particle mist formation by laser cutting is limited.

Figure 3:
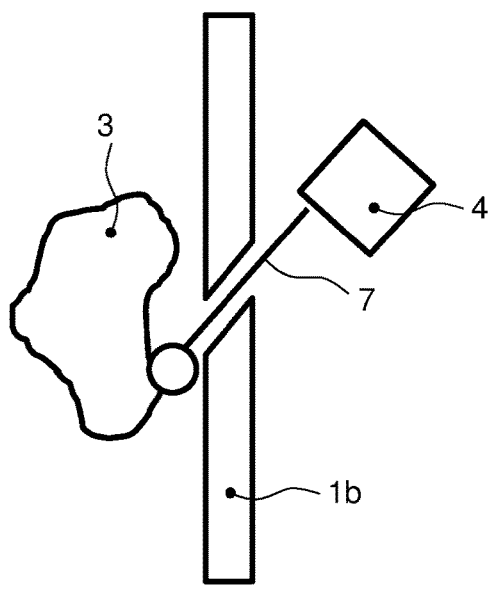
FIG. 3 illustrates an embodiment of the wall section of an embodiment of the scanning container.

The cutting can be carried out by providing the scanning container as described herein-above comprising a wall (1b) with openings (7) such as slits, through which the mechanical cutter and/or a laser beam can reach the scrap metal (3) within the scanning container (see FIG. 3 for embodiments including laser cutting). The mechanical cutter and/or laser cutter can advantageously individually and independently be located on robotic arms to automate the cutting and optional scanning process.

Figure 2:
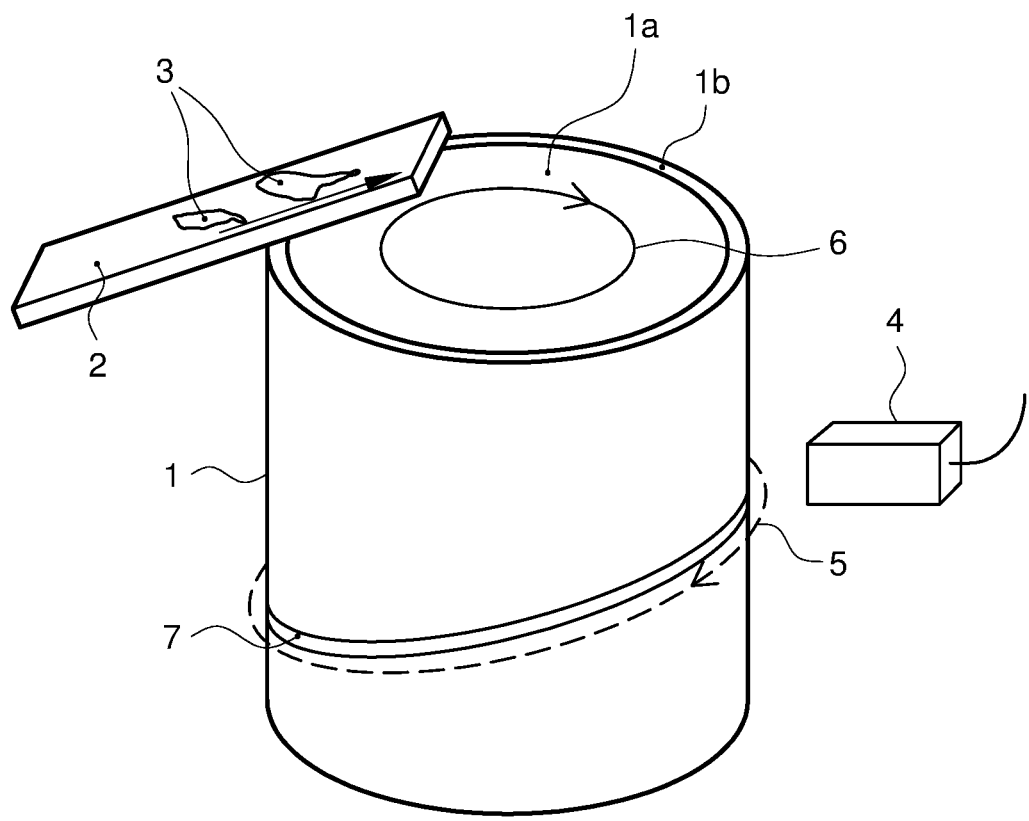
FIG. 2 shows the perspective view of an embodiment of the scanning container.
Figure 4:
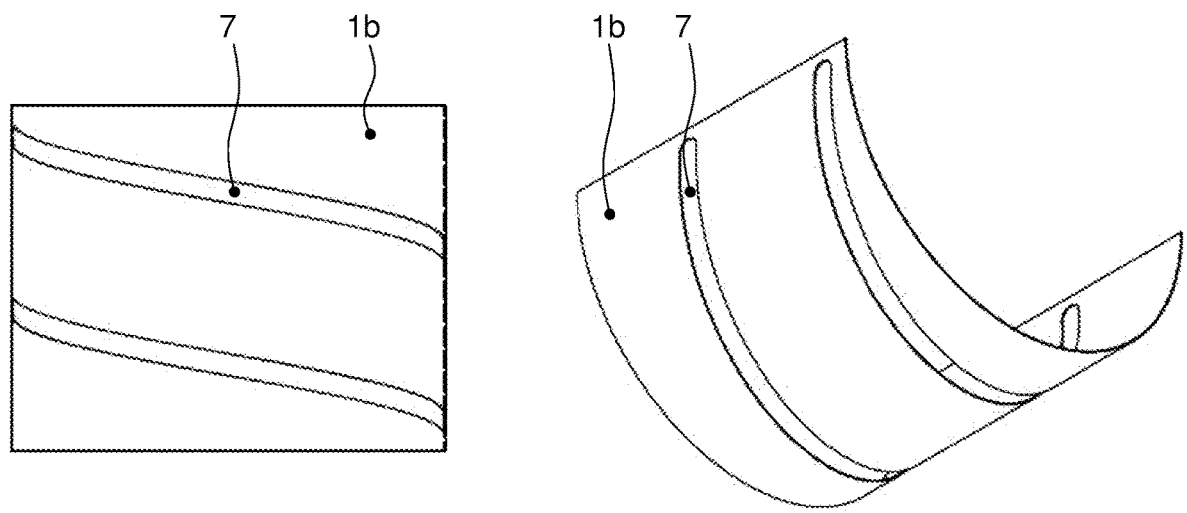
FIG. 4 illustrates an embodiment of the wall section of an embodiment of the scanning container.

FIGS. 3 and 4 illustrate a particular embodiment of a wall section (1b) of the scanning container comprising spirally-shaped slits (7) through which a laser beam and/or a mechanical cutter may reach the scrap metal. The slits may be present in various shapes. For instance, as illustrated in FIGS. 2 and 4, the slits may comprise spirally-shaped or diagonal slits. In another, preferred, embodiment, the slits comprise essentially vertical slits, meaning that when the container is in use the slits extent in the same direction as the gravity. The advantage of vertical slits is that the cut created by the mechanical cutter and/or laser is believed to result in more stable cuts such that the cut remains well accessible to the scanning device. Vertical slits are therefore particularly preferred in the embodiments wherein the mechanical cutter is used in combination with a subsequent scanning device such as a laser cutter that comprises laser-induced breakdown spectroscopy (vide infra).

Preferably, a laser cutting device is used having a power of more than 500 W or more, for instance about 530 W. Higher powered laser of for instance 1 kW or more, for instance a power of about 6 kW may also be used. Scrap metal can typically be cut by the laser cutting device having 1 kW power or higher, but a preferred cutting rate is obtained with the laser cutting device having a power of about 6 kW or higher. A power of 6 kW or higher is particularly preferred for e.g. copper-based metal scrap and other high-thermally conductive materials. Examples of suitable lasers that may be used for the laser cutting include a lamp-pumped neodymium-doped yttrium aluminum garnet (Nd:YAG) rod laser and a diode-pumped disk laser.

The laser cutting is preferably carried out in a pulsed manner, meaning that a pulsed laser beam is used. A series of pulses provided by one or more laser devices create a cut in the scrap metal. The laser cutting is preferably carried out in a rate such that about 0.01-0.10, preferably about 0.02-0.04 cubic centimeters scrap metal is removed per second ($cm^3/s$). This provides sufficient material for the determination of scrap metal content, without unnecessarily sacrificing too much scrap metal.

In a preferred embodiment, the laser cutting in accordance with the present invention comprises collection of the scrap metal material that is cut away by in the laser cutting as a mist of particles (e.g. by suction) and analysis thereof by standard techniques such as X-ray fluorescence (XRF). XRF provides a desired accuracy for the scrap metal composition determination.

In addition or alternative to XRF, spectroscopic analysis of the flame that is created during the laser cutting may be carried out. In a more preferred embodiment, the laser cutting comprises laser-induced breakdown spectroscopy (LIBS), wherein a pulsed or alternating laser is used to alternatingly cut away part of the scrap metal and analyze the plasma that is created by the laser. LIBS typically comprises directing a laser pulse to the surface of a piece of scrap metal material to create a small flame of plasma (typically 0.5 mm in size) from the surface material, which plasma (generally after cooling down and becoming transparent) can be analyzed by a spectrometer that may detect emission lines characteristic for the atoms and ions in the plasma. The amplitudes of the various emission lines as detected by the spectrometer are then interpreted into a chemical composition of the material.

For the LIBS-based laser cutting, particularly good results are obtainable if the laser settings (e.g. laser pulse frequency and/or pulses per dot) and/or the spectroscopy settings (e.g. sensitivity and/or frequency) are adjusted during the scanning, depending on the detected composition of the scrap metal. This enables efficient cutting and/or recording of particular good spectra.

Figure 5:
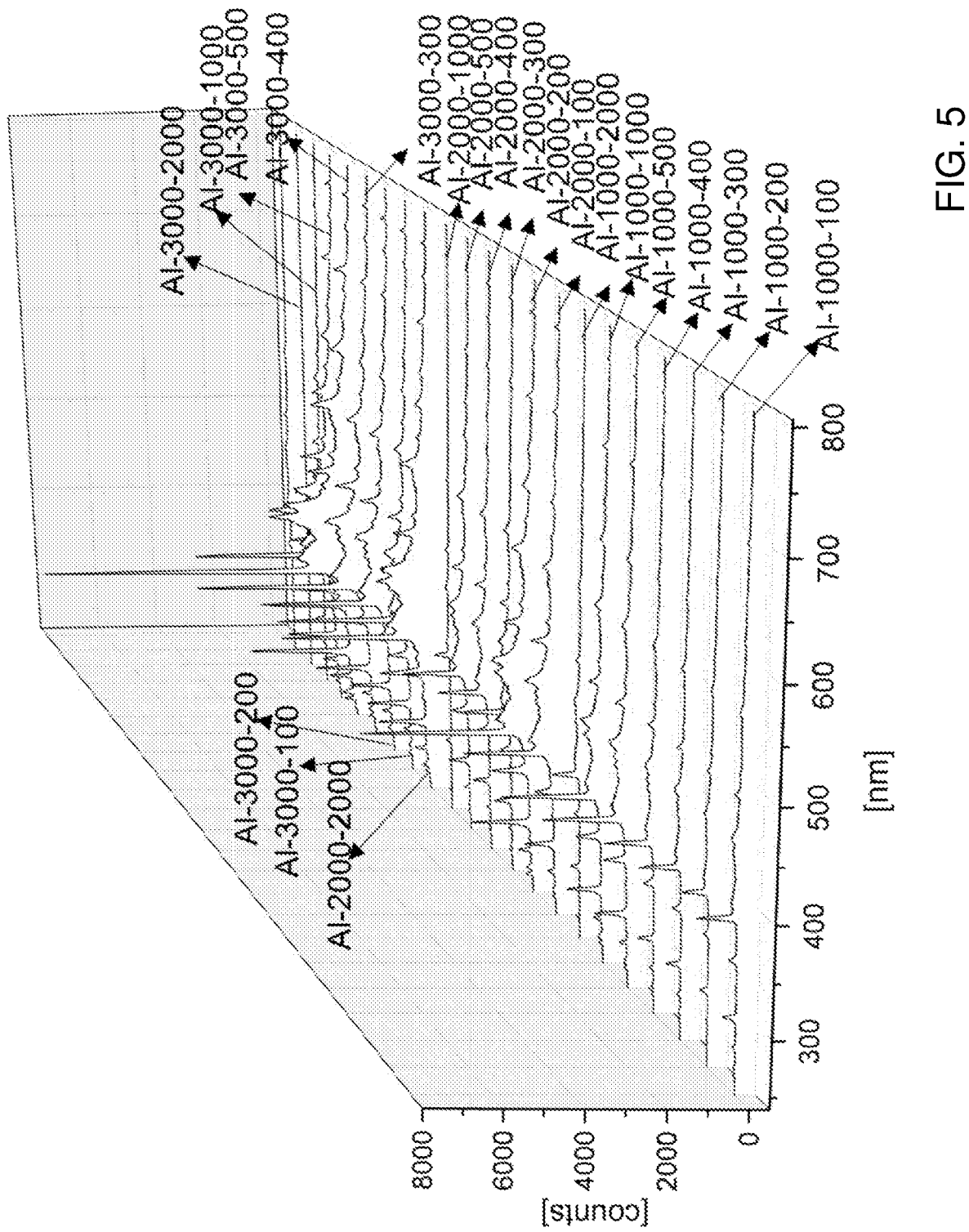
FIG. 5 provides spectra of aluminum-comprising scrap metal obtained with a pulsed Nd:YAG laser.
Figure 6:
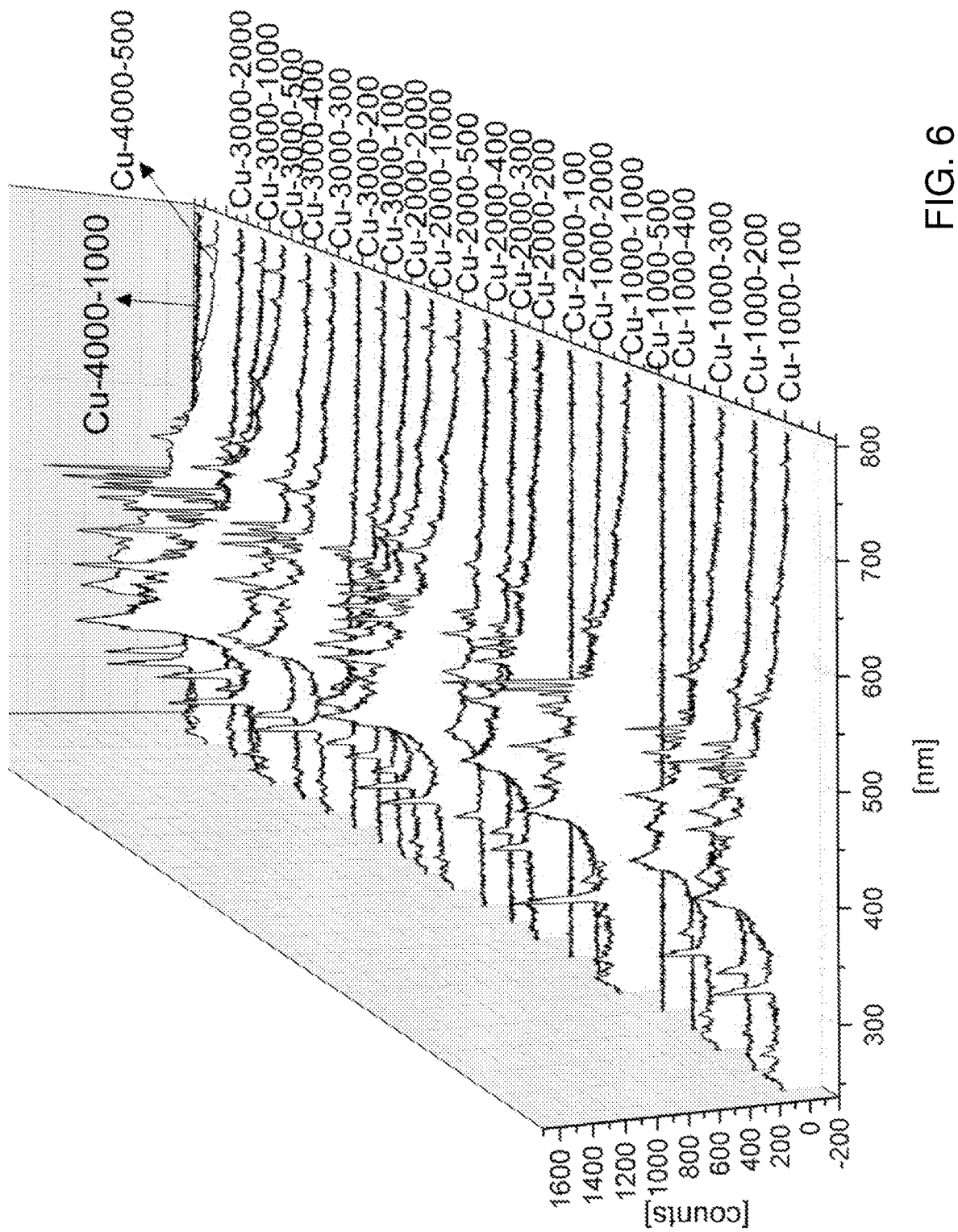
FIG. 6 provides spectra of aluminum-comprising scrap metal obtained with a pulsed Nd:YAG laser.

FIGS. 5 and 6 illustrate the advantage of adjusting the laser pulse frequency and number of pulses per dot when detecting aluminum and copper, respectively.

In FIG. 5, spectra are provided of aluminum-comprising scrap metal obtained with a pulsed Nd:YAG laser having a frequency varying from 1000-5000 Hz and a spot diameter of 0.05 mm. The Al-xxxx-yyy notation indicates detected aluminum obtained by a laser frequency of xxxx Hz, using yyy pulses per dot.

In FIG. 6, spectra are provided of copper-comprising scrap metal obtained with a pulsed Nd:YAG laser having a frequency varying from 1000-5000 Hz and a spot diameter of 0.05 mm. The Cu-xxxx-yyy notation indicates detected copper obtained by a laser frequency of xxxx Hz, using yyy pulses per dot.

Figure 7:
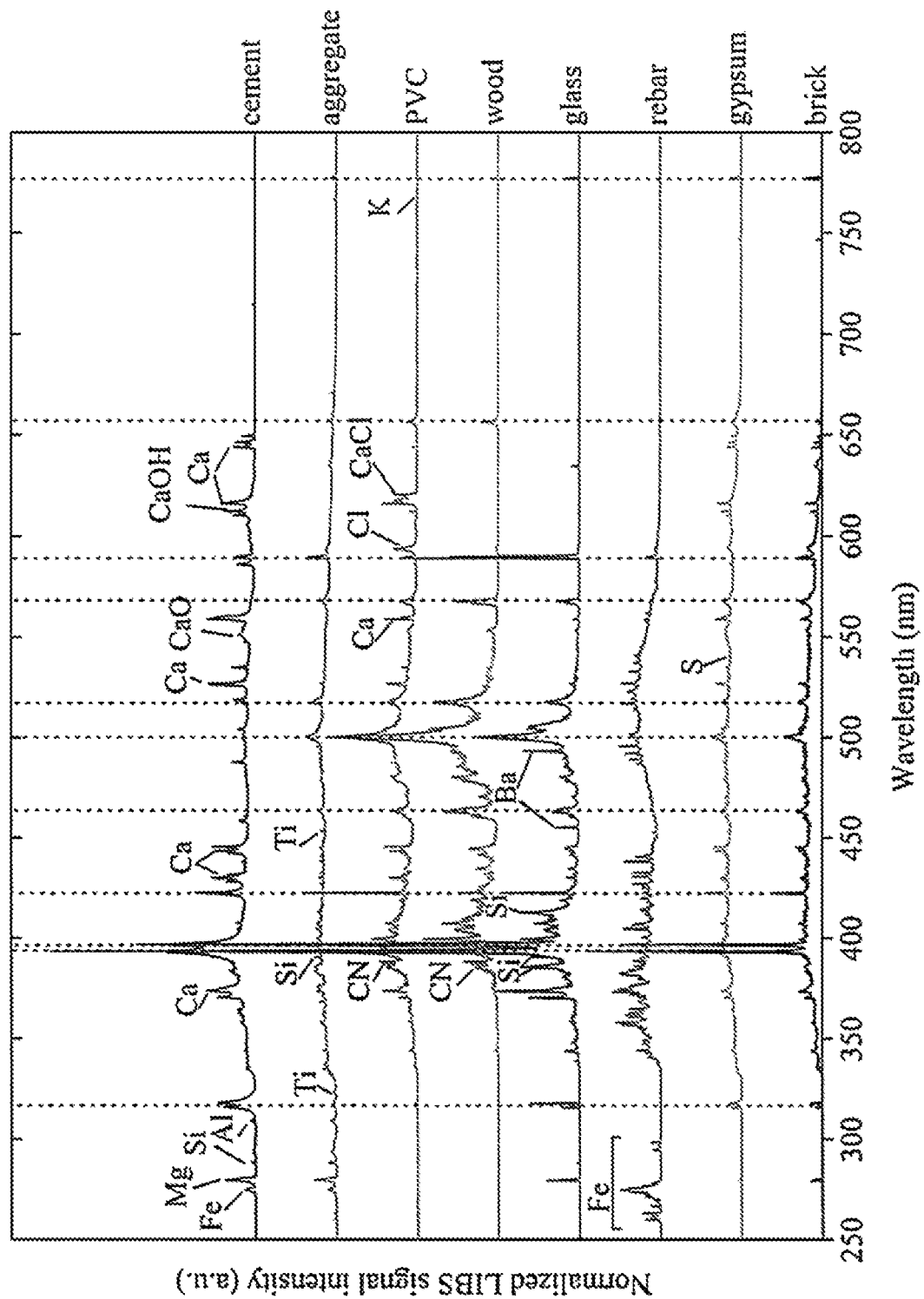
FIG. 7 illustrates the advantage of LIBS where Normalized LIBS signal intensity is plotted against wavelength (nm).

As illustrated in FIG. 7. A particular advantage of LIBS is the broad range of materials that can quantitatively be detected. For instance, LIBS enables the detection of metals such as aluminum, zinc, copper, iron and the like, as well as minerals such as calcium- and silicon-based materials, cement, aggregate, wood, glass, rebar, gypsum, brick etc. In addition, LIBS allows the quantitative detection of polymers such as polyvinylchloride (PVC) via the chlorine atoms that are present therein.

In a preferred embodiment of the present invention, the laser cutting is preferably carried out such that combustion of part of the scrap metal is prevented. Combustion of the scrap metal may result in a reduced accuracy of the scrap metal content determination by the laser cutting. The risk of combustion of the scrap metal may be lowered by reducing the oxygen level in the air, for instance by (local) nitrogen gas flushing.

In a particular embodiment of the present invention, laser scanning is combined with the low-intensity neutron scattering. As described herein above, the multiplication factor that is used in low-intensity neutron scanning may vary per type of material. The composition of the scrap metal as determined by laser cutting, can be used to select an appropriate multiplication factor. For instance, the multiplication factor for polyvinylchloride (PVC) materials is typically in the range of 16 to 20. In case the scrap material comprises PVC, the uncertainty of the low-intensity neutron scattering can be reduced by the results obtained from the laser cutting. Similarly, combining the results obtained by magnetic sensing and the laser cutting, typically also further increases the accuracy of the scanning.

It is preferred that the scanning comprises scanning of at least part of the internally placed scrap metal that is obstructed from sight upon visual inspection of the three-dimensionally packed scrap metal. A particular advantage of the above described analytic techniques (i.e. magnetic sensing, low-intensity neutron scattering and laser cutting), is that part of the scrap metal that is obstructed from sight, for instance by a coating or other scrap metal pieces, can be analyzed. The magnetic field and neutron radiation can penetrate certain parts of the scrap metal relatively easy and the laser cutting enables cutting away parts of the scrap metal to reach deeper into the three-dimensional arrangement of scrap metal (for instance up to about 0.2 meter or further) for the analysis thereof. Analyzing parts of the scrap metal that is obstructed from sight is particularly beneficial in case the composition of part of the scrap metal varies with the depth of the scrap metal. For instance, if the scrap metal comprises electric cables, the surface of the scrap metal comprises polymers, while the internal part comprises the valuable copper.

The relative ease of which the laser can cut away parts of the scrap metal and/or the final penetration depth of the laser are preferably also taken into account for determining the overall or average composition of the scrap metal.

In a preferred embodiment of the present invention, the steps of preparing the scrap metal input for scanning and scanning at least part of the scrap metal are carried out in an automated manner. This improves the repeatability of the content determination.

In case the bulk scanning of at least part of the scrap metal is (partially) based on individual measurements of a part of the scrap metal (as may be the case in for instance low-intensity neutron scattering and laser scanning), it is preferred that more than one measurement is taken to improve the accuracy of the scanning. The preferred number of measurement depend i.a. on the amount of the ferrous and/or non-ferrous metal in the scrap metal which is to be determined. Typically, at least 50, preferably at least 100, more preferably at least 500, most preferably at least 1000 individual measurements are taken per batch of the scrap metal. The high number of individual measurements, if applicable, renders the present scanning method a bulk scanning method in view of a single scan that is for instance carried out with a handheld scanning device.

A further aspect of the present invention is the bulk scanning apparatus that is especially suitable for carrying out the method of the present invention as described herein. The bulk scanning apparatus comprises the scanning container together with a low-intensity neutron scattering device, a laser cutting device and/or magnetic sensing device.

The bulk scanning apparatus of the present invention preferably comprises a laser cutting device, more preferably in combination with a low-intensity neutron scanning device and a magnetic sensing device.

In a particularly preferred embodiment, the bulk scanning apparatus comprises a scanning container which is based on a non-magnetic material such as aluminum or austenitic steel.

The scanning container may comprise an inclined raised edge on top of its wall, such that the upper part of the container that comprises the opening of the container through which the scrap metal is loaded may be funnel shaped. This facilitates the loading and allows the body of the container in which the scrap metal is collected to be sufficiently narrow such that the scrap metal can appropriately arranged in the container for its subsequent scanning.

In another preferred embodiment, the scanning container is cylinder-shaped and comprises a wall that comprises one or more openings such that the laser cutting device that is positioned outside the scanning container project a laser beam inside the scanning container through one or more openings, as for instance illustrated in FIGS. 2, 3 and 4.

It may be possible that the improved preparation of the scrap metal input for submissions to the bulk scanning apparatus, in particular reorganizing said input to obtain a substantially predictable reorganized arrangement and the specific embodiments thereof as described herein, may also advantageously be applied to methods for the bulk determination of scrap metal content that to not comprise securing the scrap metal. This also applies to the scanning methods as described herein, in particular to the magnetic sensing, low-intensity neutron scattering, laser cutting and combinations thereof, as well as the specific embodiments as described herein above. For certain aspect of the present invention, securing the scrap metal may thus not be essential, but merely preferred.

A further aspect of the present invention is accordingly the standardization and/or certification of the method and the scanning device in accordance with the present invention. As described in part herein-above, the method of the present invention is preferably standardized and certificated, meaning that the steps and scanning devices for the method are standardized. Standardization, certification and control thereof can contribute to the overall securing of the present method and the perceived reliability of the determination of the scrap metal content.

The verification or control of whether methods and scanning devices in accordance with the present invention meet the standardization and/or certification requirements, is another aspect of the present invention. Said verification or control can be carried out by providing a scrap metal input of which the content is known, and verify whether the determination by the verified standardized or certified method of scanning device meets the standardization and/or certification requirements. This aspect of the present invention has the advantage that the reliability and accuracy of the scanning of scrap metal in the overall scrap metal handling process is improved. This reduces possible discussions between parties on the correctness on the assessment, the requirement of reassessments being carried out, and possible discussion on which assessment should be accepted.

The standardization, certification and verification or control thereof in accordance with the present invention, thus improves and secures the present method for the bulk determination of scrap metal content.

For the purpose of clarity and a concise description features are described herein as part of the same or separate embodiments, however, it will be appreciated that the scope of the invention may include embodiments having combinations of all or some of the features described.

The invention claimed is:

1. A method for the bulk determination of scrap metal content, said method comprising the steps of
providing a scrap metal input;
preparing said input for submission to a bulk scanning apparatus;
scanning at least part of the scrap metal with a bulk scanning apparatus to determine the composition of the scrap metal by low-intensity neutron scattering; and
securing said scrap metal from the step of providing the scrap metal input to the step of scanning at least part of the scrap metal by at least one of keeping the scrap metal in a sealed room or container, monitoring the scrap metal, and labeling the scrap metal.

2. The method according to claim 1, wherein the step of preparing said input comprises reorganizing said input to obtain a substantially predictable reorganized arrangement comprising the scrap metal.

3. The method in accordance with claim 1, wherein the scrap metal comprises ferrous and/or non-ferrous scrap metal.

4. The method in accordance with claim 1, wherein the scrap metal further comprises one or more contaminants selected from the group consisting of moisture, plastics, oil, steel, minerals or combinations thereof; and determining the composition of scrap metal comprises determining the ferrous or non-ferrous metal content versus contaminants content.

5. The method in accordance with claim 1, comprising subsequent to the step of scanning, loading the scrap metal into a transportation container and sealing the loaded transportation container, wherein said method preferably further comprises further securing, preferably visually monitoring, of said scrap metal from the step of scanning to the step of loading the scrap metal into the container.

6. The method according to claim 1, further comprising comparing the composition of the scrap metal as determined in the scanning step with the composition of the scrap metal as determined in a separate previous scanning step, wherein the separate previous scanning step was carried out using a scanning apparatus of the same type as said bulk scanning apparatus, preferably using a substantially identical bulk scanning apparatus.

7. The method in accordance with claim 1, wherein the securing of the scrap metal comprises safe guarding the scrap metal against undetected tampering, monitoring, preferably visually monitoring the scrap metal, tagging or labeling the scrap metal, monitoring the environment of the scrap metal, or a combination thereof.

8. The method in accordance with claim 1, wherein the step of preparing said input for submission to a bulk scanning apparatus comprises arranging said input in a three-dimensionally arrangement, preferably arranging said input in a scanning container.

9. The method in accordance with claim 1, wherein the scanning comprises scanning of at least part of the scrap metal that is obstructed from sight upon visual inspection of the scrap metal.

10. The method in accordance with claim 1, wherein the scanning comprises cutting, magnetic sensing, low-intensity neutron scattering, or a combination thereof, preferably mechanical cutting and laser cutting, more preferably mechanical cutting and laser cutting comprising laser-induced breakdown spectroscopy.

11. The method in accordance with claim 10, wherein the magnetic sensing comprises placing at least part of the scrap metal in a magnetic field ranging from 5 to 100 Gauss, preferably 10 to 40 Gauss and detecting magnetic field changes by one or more Hall sensors.

12. The method in accordance with claim 10, wherein the low-intensity neutron scattering comprises determining content of hydrogen atoms in at least part of the scrap metal.

13. The method in accordance with claim 1, wherein the step of scanning comprises more than 50, preferably more than 100, more preferably more than 500, most preferably more than 1000 independent measurements of the scrap composition.

14. An apparatus for reorganizing and scanning a scrap metal input according to the method of claim 1, said apparatus comprising a scanning container configured for receiving scrap metal and a low-intensity neutron scattering device.

15. The apparatus in accordance with claim 14, wherein the scanning container is cylinder-shaped and comprises a wall that comprises one or more openings such that during operation, the laser cutting device that is positioned outside the scanning container can project a laser beam inside the scanning container through one or more openings.

16. The apparatus of claim 14, further comprising a magnetic sensing device.

17. The apparatus of claim 16, further comprising a laser cutting device.

* * * * *